US011510616B2

(12) United States Patent
Kopperschmidt et al.

(10) Patent No.: US 11,510,616 B2
(45) Date of Patent: Nov. 29, 2022

(54) APPARATUS FOR IDENTIFYING AND MANIPULATING A BLOOD VESSEL, AND CORRESPONDING METHOD

(71) Applicant: FRESENIUS MEDICAL CARE DEUTSCHLAND GMBH, Bad Homburg (DE)

(72) Inventors: Pascal Kopperschmidt, Dittelbrunn (DE); Pia Daniel, Bodman (DE); Reiner Spickermann, Wasserlosen-Burghausen (DE); Otto Arkossy, Budapest (HU); Cacilia Scholz, Schwalbach (DE); Kai-Uwe Ritter, Rednitz-Hembach (DE); Elke Schulte, Schweinfurt (DE); Christopher Hauke, Mainz-Kostheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 557 days.

(21) Appl. No.: 16/480,681

(22) PCT Filed: Jan. 29, 2018

(86) PCT No.: PCT/EP2018/052147
§ 371 (c)(1),
(2) Date: Jul. 25, 2019

(87) PCT Pub. No.: WO2018/138342
PCT Pub. Date: Aug. 2, 2018

(65) Prior Publication Data
US 2019/0380645 A1    Dec. 19, 2019

(30) Foreign Application Priority Data

Jan. 30, 2017 (DE) .................. DE10 2017 201 440

(51) Int. Cl.
*A61B 5/00* (2006.01)
*A61B 5/15* (2006.01)
(Continued)

(52) U.S. Cl.
CPC .......... *A61B 5/489* (2013.01); *A61B 5/15003* (2013.01); *A61B 5/1535* (2013.01); *A61B 5/022* (2013.01); *A61B 5/150786* (2013.01)

(58) Field of Classification Search
None
See application file for complete search history.

(56) References Cited

U.S. PATENT DOCUMENTS 4,738,249 A   4/1988  Linman et al.
5,647,373 A   7/1997  Pltieli
(Continued)

FOREIGN PATENT DOCUMENTS

CN   101171046 A   4/2008
CN   105726062 A   7/2016
(Continued)

OTHER PUBLICATIONS

Jaberi et al., "Arteriovenous Fistulas for Hemodialysis: Application of High-frequency US to assess vein wall morphology for cannulation readiness" Radiology, 2011, vol. 261, No. 2, pp. 616-625. (Year: 2011).*
(Continued)

*Primary Examiner* — Yi-Shan Yang
(74) *Attorney, Agent, or Firm* — Kilyk & Bowersox, P.L.L.C.

(57) ABSTRACT

The invention relates to a detection apparatus and a method for detecting and manipulating a blood vessel under the skin of part of the body of a patient, which comprises a treatment chamber for accommodating the body part, a data processing control device, a vascular structure measuring device for
(Continued)

detecting the position and/or dimensions of vascular structure data of the blood vessel in the treatment chamber by measurement, a vascular manipulation device for changing the position and/or dimension of the blood vessel, wherein the control device is designed to control the vascular manipulation device as a function of the vascular structure data.

10 Claims, 12 Drawing Sheets

(51) Int. Cl.
  *A61B 5/153* (2006.01)
  *A61B 5/022* (2006.01)

(56) References Cited

U.S. PATENT DOCUMENTS

| | | | |
|---|---|---|---|
| 8,888,714 B1 | 11/2014 | Soto | |
| 2004/0171923 A1 | 9/2004 | Kalafut et al. | |
| 2007/0166345 A1 | 7/2007 | Pavcnik et al. | |
| 2008/0146939 A1 | 6/2008 | McMorrow et al. | |
| 2008/0195043 A1 | 8/2008 | Schwach et al. | |
| 2008/0275396 A1 | 11/2008 | Neerken et al. | |
| 2009/0234261 A1 | 9/2009 | Singh | |
| 2012/0190981 A1 | 7/2012 | Harris et al. | |
| 2015/0065916 A1* | 3/2015 | Maguire | A61B 34/32 600/573 |
| 2015/0133791 A1 | 5/2015 | Sato et al. | |
| 2015/0374273 A1 | 12/2015 | Maguire et al. | |
| 2016/0249990 A1 | 9/2016 | Glozman et al. | |
| 2016/0310149 A1* | 10/2016 | Downey | A61B 17/1355 |
| 2017/0035335 A1* | 2/2017 | Breteau | A61M 5/427 |
| 2018/0220944 A1* | 8/2018 | Otsubo | A61B 5/150343 |

FOREIGN PATENT DOCUMENTS

| | | |
|---|---|---|
| FR | 3019724 A1 | 10/2015 |
| WO | 2010029521 A2 | 3/2010 |
| WO | 2013180126 A1 | 12/2013 |
| WO | 2016087123 A1 | 6/2016 |

OTHER PUBLICATIONS

International Search Report and Written Opinion issued in corresponding International Patent Application No. PCT/EP2018/052147 (with English translation of International Search Report) dated May 4, 2018 (15 pages).

Office Action issued in corresponding German Patent Application No. 10 2017 201 440.7 dated Aug. 31, 2017 (6 pages).

Chen et al., "Real-time Needle Steering in Response to Rolling Vein Deformation by a 9-DOF Image-Guided Autonomous Venipuncture Robot," IEEE/RSJ International Conference on Intelligent Robots and Systems (IROS) Congress Center Hamburg, Sep. 28-Oct. 2, 2015, Hamburg, Germany, pp. 2633-2638.

Chen et al., "Developing the World's First Portable Medical Robot for Autonomous Venipuncture," IEEE Robotics & Automation Magazine, Mar. 2016, pp. 10-11.

Cheng et al., "A venipuncture detection system for robot-assisted intravenous catheteriation," 6th IEEE RAS/EMBS International Conference on Biomedical Robotics and Biomechatronics (BioRob), Jun. 26-29, 2016, UTown, Singapore, pp. 80-86.

International Preliminary Report on Patentability issued in corresponding International Patent Application No. PCT/EP2018/052147 dated Aug. 8, 2019 (9 pages).

English-language translation of office action dated Dec. 21, 2022, issued by the Japan Patent Office, for application No. JP 2019-541127, Dispatched on Jan. 4, 2022 (2 pages).

* cited by examiner

APPARATUS FOR IDENTIFYING AND MANIPULATING A BLOOD VESSEL, AND CORRESPONDING METHOD

This application is a National Stage Application of PCT/EP2018/052147, filed Jan. 29, 2018, which claims priority to German Patent Application No. 10 2017 201 440.7, filed Jan. 30, 2017.

The present invention relates to the field of medical technology and in particular to a detection apparatus for detecting and manipulating a blood vessel under the skin of a part of the body of a patient, a cannulation robot having a detection apparatus, and a corresponding method for the automated detecting and manipulating of a blood vessel under the skin of part a patient's body.

The puncturing of blood vessels, also known as cannulation, is a routine procedural step in the medical treatment of many patients in which a fluid connection, in particular a cannula, is established between a patient's blood circulation and an external fluid system. Cannulation is usually performed by physicians or trained personnel. The quality of the vascular access created by the cannulation thereby depends on a plurality of parameters which are in particular affected by the individual and temporally varying abilities of the medical personnel and the physical characteristics of the patients to be treated as well as the diversity of the technical instruments used in cannulation.

Being a routine procedure in many treatments, cannulation is also frequently performed. In order to thereby standardize cannulation, make efficient use of financial as well as personnel resources, and reliably ensure high treatment quality, cannulation robots have been developed which autonomously perform a cannulation procedure on patients using suitable sensor technology and motor function. Such cannulation robots and the technical resources thereby used are known from e.g. EP 0 654 244 B1, US 2015/0065916 A1 and WO 2015/052719 A1. Detection apparatus for detecting vascular structures are known on these types of robots.

The invention is based on the task of specifying an improved detection system, in particular to further automate cannulation, which enables a more efficient vasculature treatment subsequent the detection.

The invention respectively solves this task by a detection apparatus in accordance with the teaching of independent claim 1 and a method in accordance with the teaching of independent claim 11. Preferential embodiments, further developments or variants in particular constitute the subject matter of the independent claims. The subject matter of the claims is expressly made a part of the specification disclosure.

The detection apparatus according to the invention provides the advantage of being able to manipulate and thus optimize an initially detected position and/or physical dimensions of the blood vessel in a desired manner. In particular, a blood vessel exhibiting physiological or pathological-based changes can be manipulated so as to enable a subsequent treatment, in particular automatic cannulation.

The vascular structure measuring device is designed to detect blood vessel position and/or dimensions by measuring the vascular structure data of the blood vessel in the treatment chamber. Measuring the position and/or dimensions of the blood vessel in the form of vascular structure data and the subsequent manipulation of said position and/or dimensions by means of the vascular manipulation device serves preferably in preparation for a potentially ensuing treatment of the patient, in particular the subsequent automatic cannulation of the blood vessel. The manipulation hereby serves in particular as a corrective measure in order to induce a desired improvement of the position and/or dimensions of the blood vessel.

The vascular structure data is in particular evaluated as to whether the position and/or dimensions of the blood vessel correspond to at least one criterion. Said criterion can be particularly of importance to the subsequent treatment of the patient, in particular the question of whether such a treatment is feasible and/or which treatment modification is to be performed. Manipulating the blood vessel with the vascular manipulation device changes the position and/or dimension and the criterion is then rechecked after the manipulation. The invention is particularly advantageous in cases in which the blood vessel in the initial position and/or the initial dimension—thus in particular prior to the manipulation—did not satisfy the at least one criterion and the ensuing manipulation serves the purpose of subsequently fulfilling said criterion. The manipulation can for example provide for stemming blood flow in the blood vessel by way of a hemostasis device which leads to a swelling of the blood vessel and results in a predetermined blood vessel thickness sufficient enough for automatic cannulation to be reliably performed.

Reference is for the most part made to "the" blood vessel in the present document, thus in singular. However, the invention relates just as equally to the detection and manipulation of more than one blood vessel.

The vascular structure data, which contains information on the position of a blood vessel, can contain the position data with which the spatial area or a change in the spatial area can be clearly determined, same being taken from said spatial area. This position data can be defined to at least one fixed point of reference of the detection apparatus or a fixed point of reference of the treatment apparatus, in particular the cannulation robot which optionally comprises the detection apparatus. Alternatively, it is also feasible for the position to be detected using this vascular structure data such that only the positional data of the blood vessel tunic is stored, thus for example the course of the blood vessel wall which channels the blood. Further alternatively, or additionally, it is also feasible for the position to be detected using this vascular structure data such that the positional data of the spatial area perfused by the flowing blood is detected, which is for example possible in the case of detecting positional data via Doppler ultrasound measurements. The position data can thus also be alternatively or additionally stored as velocity data.

Instead of—or additionally to—such absolute positional data, absolute positional data can contain changes in blood vessel position as relative positional data.

The vascular structure data, which contains the information on the dimensions of a blood vessel, can in particular contain information on the thickness of the blood vessel or the thickness of the spatial area of the blood vessel perfused by the blood, measured perpendicular to the direction of flow, thus longitudinally, in particular measured parallel to the skin surface of the patient's body part, and/or in particular measured perpendicular to the skin surface of the patient's body part.

The vascular structure data can also contain approximation data on the position and/or dimensions of the blood vessel by, for example, only detecting positional data or distance data section by section and/or at a reduced resolution while the position and/or dimensions of the blood vessel are estimated with the requisite accuracy and supplemented by applying a model, e.g. by way of an interpolation procedure.

The vascular structure measuring device can be configured as an image capture device so that image data of the at least one blood vessel, preferably a group of several blood vessels, can be recorded as vascular structure data. The vascular structure data is preferably stored in a data storage device, which can be part of the detection apparatus. The vascular structure data is thereby available for subsequent evaluation and can optionally also be stored permanently, in particular assigned to a patient as patient data, and pulled up again for later use in the course of for example a lengthier treatment, in particular in the case of a chronic illness.

The vascular structure measuring device, in particular the image capture device, can be equipped for optical measurement. Referred to as an image is in particular a data set containing information on the position and/or spatial dimensions of the at least one blood vessel. The image capture device thereby preferably comprises one or more optical sensors or at least one camera, by means of which one or more visible light wavelength range image recordings; i.e. between 380 and 780 nm, can be created and digitally saved. The vascular structure measuring device, in particular the image capture device, can in particular also be equipped to measure in other electromagnetic spectrum ranges, in particular in the ultraviolet range, i.e. between 100 nm and 380 nm, or in the infrared range, i.e. between 780 nm and 1 mm, preferably additionally or alternatively to measuring in the visible spectrum. The contrast can thereby be adapted. Optical detection of blood vessels is described for example in WO 2010/029521 A2.

Alternatively, the vascular structure measuring device, in particular the image capture device, can be equipped for computer tomography (CT), magnet resonance tomography (MRT) or positron emission tomography (PET) measurements.

The vascular structure measuring device, in particular the image capture device, is preferably equipped for ultrasound—in particular sonographic—measurements, in particular duplex and/or Doppler procedure measurements. Images can thereby be cap-tured with relatively low equipment expenditure. Detecting blood vessels using ultrasound is an established procedure and described for example in US 2008/0146939 A1.

Preferably, the vascular structure measuring device, in particular the image capture device, is configured for repeated measuring of the position and/or dimensions of the blood vessel, in particular for measurements repeated in phases or continuously, in particular at a given temporal frequency. A frequency of for example one measurement per second (1 Hz) or greater affords precise detection of the position and/or dimensions of the blood vessel and thus better control for the ensuing vascular manipulation so that an optional subsequent treatment of the patient, in particular an automatic blood vessel cannulation, can be more precisely performed and controlled.

The detection apparatus preferably comprises a base on which preferably all the component parts of the detection apparatus are mounted, in particular the data processing control device, the vascular structure measuring device and the vascular manipulation device. Should the detection apparatus be a component part of a treatment apparatus, e.g. a cannulation robot, the base of the detection apparatus can be a component part of the treatment apparatus.

The treatment chamber can be a partly enclosed or open spatial area which can in particular be integrated into a treatment apparatus, in particular a cannulation robot. The treatment chamber serves to at least partly accommodate the part of the patient's body with the subcutaneous blood vessel to be detected. The body part is preferably an arm or a leg.

The treatment chamber preferably comprises a supporting device for supporting the body part, in particular a rest or a plurality of rests.

The treatment chamber can comprise a fixation device, by means of which the body part can be immobilized relative to the treatment chamber or relative to the supporting device and is immobilized during the detection and/or subsequent treatment, in particular cannulation. The fixation device can comprise at least one fixation strap for securing the body part to the supporting device. The fixation device can furthermore also assume the function of the supporting device, by for example the fixation device suspending the body part in the treatment chamber. The fixation preferably ensues so as to restrict the translational and/or rotational mobility of the body part in at least one, at least two, three, four, five or six spatial directions, preferably in all six spatial directions in positive and negative direction along the three orthogonal spatial axes of a Cartesian coordinate system and/or all six rotational directions around said spatial axes.

The fixation device can comprise or be formed by a cushion device. The cushion device can be designed to accommodate a fluid, in particular air, a liquid or a gel. Preferably, an electrically controllable fluid transport device can be provided to transport the fluid, in particular a pump or a pressing device. This transport is preferably automatically controlled by the control device such that the detection apparatus can preferably automatically perform the fixation. In the fixation process, it can be provided for the fluid transport device to increase the volume of fluid in the cushion device so as to restrict the mobility of the body part disposed on the cushion device and preferably immobilize same. The cushion device can partly or completely encircle the body part; in particular, the cushion device can be designed as a closed or open hose ring, similar to a cuff as used in measuring blood pressure. The cushion device serving as a supporting or fixation device is thereby preferably fixed in the detection apparatus.

The supporting device and/or the fixation device can in particular be additionally configured as a vascular manipulation device.

The vascular manipulation device is designed to change the blood vessel position and/or dimension. Preferably, the vascular manipulation device is designed as a pressing device by means of which a pressure is exerted on the part of the body disposed in the treatment chamber in order to stem the blood in the blood vessel to be detected. Stemming the blood can achieve and regulate a specific blood vessel thickness pursuant to predetermined criteria. In particular, the blood vessel thickness can be regulated by the control device.

Preferably, the pressing device comprises an electrically controllable cushion device, as described above, its fill volume and thus the applied pressure being electrically controlled by the control device. The controlling of the vascular manipulation device, in particular the pressing device or the cushion device, particularly the transmitting of control signals as well as the electrical power supply to same, can ensue via wires, whereby an electrical cable, in particular a data communication cable, can serve in the exchange of signals between the control device of the detection apparatus and the pressing device. Signals can also be exchanged wirelessly, wherein the pressing device can in this case be realized as a separate component from the detection apparatus, its power supply provided by a battery arranged in or on the vascular manipulation device. Realizing the vascular manipulation device separately can keep the treatment chamber free for other devices. Flexibly adapting to different body parts and patients of different physical builds is moreover possible. The cushion device can furthermore comprise an actuator device, by means of which the cushion device can be subjected to a tension, by for example a hose ring being circumferentially tightened so as to bind the body part and apply a force acting as radial pressure on the body part.

The vascular manipulation device can comprise a temperature control device, in particular comprising a temperature sensor, in order to warm or cool a skin-contacting region of a pressing device or preferably a fluid medium contained in a cushion device to a target temperature and in particular to regulate the setting of temperature. Warmth can open capillaries, whereby blood circulation in the skin is improved.

The pressing device can furthermore comprise one or more strap devices which—similar to a hose ring but without a fluid-filled cavity—is circumferentially tightened by one or more actuator devices of the vascular manipulation device, whereby they in particular bind the body part and apply a force acting as radial pressure on the body part.

The pressing device can furthermore comprise one or more movable clamping arms which can be movably mounted in the treatment chamber, in particular movably mounted on the supporting device or fixation device. The one or more movable clamping arms can preferably be moved by one or more actuator devices of the vascular manipulation device in order to apply the desired contact pressure on the body part. The section of tissue containing the blood vessel can thereby be pressed in a radially outward direction away from the body part between the ends of the retaining clamps, whereby the desired blood stemming is on the one hand achieved and, on the other, the blood vessel is accessible and also immobilized.

Moreover, the vascular manipulation device comprising the at least one retaining clamp can be configured to apply a tension to the skin under which the blood vessel to be detected is located, by the clamping arms having adhesive contact points which make contact with and adhesively hold the skin so that a pulling motion of the retaining clamps tautens the skin positioned between the contact sections of the retaining clamps. This can thereby, on the one hand, immobilize the blood vessel to be detected. On the other hand, its position can be manipulated by moving the retaining clamps adhering to the skin. The contact sections can effect the adhesion particularly by means of a friction-inducing material applied to the contact section, e.g. silicone elastomer, or by an adhesive section applied to the contact section.

The pressing device can furthermore comprise a movable manipulation device, in particular a holding device for a tool, e.g. a robotic arm, by means of which a pressing head serving as a tool is placed onto the body part and the desired pressure exerted. The contact area of the pressing head can in particular amount to between one and several square centimeters so that a relatively localized pressure can in particular be applied to the body part. Thus, in particular only one single blood vessel or a smaller number of blood vessels can be stemmed to the desired extent, thereby enabling gentle treatment. The contact area can additionally comprise a force sensor in order to be able to control the contact pressure thereto—additionally to the measurement provided by the vascular structure measuring device. The contact area can amount in particular to between 1 $cm^2$ and 100 $cm^2$, particularly between 1 $cm^2$ and 50 $cm^2$, preferentially between 1 $cm^2$ and 10 $cm^2$.

The pressing device can comprise a force sensor to measure the contact pressure. The value of the contact pressure, in particular that which exists when the patient blood vessel to be detected reaches the desired—position and/or dimension-characterizing—value, can be stored in a data storage device. The data storage device can be a part of the detection apparatus or a part of the treatment apparatus, in particular the cannulation robot comprising the detection apparatus.

Preferably, the pressing device is designed to not exceed a predetermined maximum contact pressure value. This value can be determined beforehand as being the value at which the blood flow of the stemmed blood vessel is fully obstructed or restricted up to a certain value. Doing so treats the patient's body part with care. This safety device can be particularly advantageous with dialysis patients or those with other illnesses in which a blood vessel, in particular an arteriovenous fistula, needs to be punctured repeatedly and can thus be particularly sensitive to pain.

Preferably, the detection apparatus comprises a blood pressure measuring device. The pressing device can be configured as a blood pressure measuring device.

Preferably, the contact pressure is set to a value of between 40 mmHg and 100 mmHg. The contact pressure is preferably selected so as to interrupt the venous outflow through the blood vessel but not, however, the arterial inflow. It is therefore preferential for the contact pressure to be lower than the diastolic pressure.

The pressing device can be designed to repeatedly apply contact pressure, in particular by means of a contact section of the pressing device repeatedly pressing against the body part. Percussing the body part releases histamine in the skin, which leads to reddening of the skin, whereby the blood vessel(s) dilate. This manipulation also enables a better depicting of the blood vessel.

The vascular manipulation device can be designed as a heat transfer device in order to transfer warmth to the patient's body part. Warmth can improve circulation in the skin. Warmth can dilate a vessel such that a subsequent treatment, in particular an automatic cannulation, can be improved. The vascular manipulation device can in particular comprise a thermal transfer section provided to contact the skin and transfer warmth by diffusive heat transport. As described above, a cushion device can be configured as a heat transfer device by the fluid medium inside the cushion device being heated or cooled to a target temperature. The cushion device can in particular be designed as a sleeve, particularly a cuff, so that the sleeve at least partly or completely encircles the body part in at least one plane, particularly in tube-like form. Doing so can thereby achieve a particularly large-area thermal contact with the skin in order to stimulate blood circulation over a large area of tissue. Optionally, the sleeve can be inflated or respectively expanded with fluid in order to exert a contact pressure able to serve in stemming the blood flow and which can on the other hand improve thermal contact between the sleeve and the body part. The sleeve can be transparent and/or comprise a gap or opening to enable measuring by the vascular structure measuring device. The heat transfer device can in particular comprise at least one temperature control device, and preferably at least one temperature sensor, and in particular be designed to set the temperature in regulated manner.

Preferably, the heat transfer device comprises a radiant heater in order to transfer warmth to the body part by radiation. The radiant heater can be an infrared radiant heater. The radiant heater can be designed to radiate heat directed at a body part, in particular a section of the body part, in order to precisely target the application of heat. The radiant heater can be movably mounted in the treatment chamber.

The vascular manipulation device can comprise a movable supporting device to movably support the arm. To that end, the vascular manipulation device preferably comprises an actuator device, in particular an electric motor, to move the movable supporting device. This movement can be relative to the base of the detection apparatus and can be a rotational and/or translational movement. Moving the body part also enables the desired changing of the position of the blood vessel. The movement is thereby adapted to the physiological situation—the body part is not to be moved in a non-physiological manner. Such a manipulation can be useful for example to supplementarily complement the movement of the punctured cannula upon blood vessel cannulation. A non-movable supporting device is however also preferential.

The control device is designed to control the vascular manipulation device as a function of the vascular structure data obtained by the vascular structure measuring device. The measurement can occur at higher frequency than the manipulation. Preferably, the control device is designed to perform, by means of the vascular structure measuring device, a—in particular precisely one—measurement of vascular structure data and thereafter perform a—in particular precisely one—manipulation. It can for example be sufficient and provided for, subsequent to the vessel thickness being determined, the pressing device to exert exactly one contact pressure on the body part corresponding to an empirical value at which such a blood vessel experiences stemmed blood flow and thus dilates so that it is particularly suitable for puncture. The contact pressure can be patient-individual and can additionally be individually selected for the patient's blood vessel by, for example, extracting historical patient data, which can in particular also contain vascular structure data.

Preferably, the control device is designed to regulate the vascular manipulation device as a function of the vascular structure data. The regulation specifies a specific blood vessel position and/or dimension as a predefined target value of a control loop. The position and/or dimension of the blood vessel are documented as measured variables of the control loop. A parameter, by means of which the vascular manipulation device is controlled, serves as the control variable of the control loop. The parameter can be a parameter characterizing the contact pressure, by means of which the degree of action of a vascular manipulation device designed as a pressing device is determined. The repeated measurements and manipulations provided for the regulation allows a particularly precise adjusting of blood vessel position and/or dimensions.

Preferably, the detection apparatus is designed to store the value characterizing the vascular manipulation, in particular the value of the contact pressure, after the manipulation has been performed. This value is in particular that which exists when the patient blood vessel to be detected reaches the desired—position and/or dimension-characterizing—value. It can be stored in a data storage device and can in particular be stored as part of the patient data.

Preferably, the control device is designed to perform the change or the regulating of the position and/or dimensions of the blood vessel within a predetermined time interval, in particular a time interval of less than 60 seconds, preferably less than 30 seconds, preferably less than 20 seconds, preferably less than 10 seconds. If the manipulation compresses the blood vessel, a limited, in particular short manipulation time prevents a non-physiological strain on the body part. Preferably, a subsequent cannulation—by using the detection apparatus in a cannulation robot—is also performed within the cited time interval in order to keep the manipulation and thus the physical stressing of the body part as short as possible. It is known that certain blood values can change over longer periods of stasis, which can in particular be undesirable for subsequent blood diagnostics.

Preferably, the detection apparatus according to the invention or one of its embodiments described herein is a component part of a treatment apparatus, in particular a cannulation robot. The cannulation robot, respectively the control device of the cannulation robot, is thereby preferably designed to automatically perform the cannulation of the blood vessel detected and changed by way of the detection apparatus, after the position and/or the dimensions of the blood vessel have been effected as desired. A treatment apparatus can further carry out a non-invasive treatment of the blood vessel.

The detection apparatus can be designed to record at least one image of the vascular structure prior to, during and/or after the manipulation of the blood vessel by the vascular manipulation device, for example by means of an image capture device provided in the vascular structure measuring device, and to store this at least one image in a data storage device as vascular structure data. In this case, the manipulation serves to improve the visual representation of the vascular structure. Such vascular structure data can be used to verify healthy development of a vascular structure, in particular a fistula.

The detection apparatus, respectively the control device of the detection apparatus, can be designed to access stored patient data—particularly in a patient database—in order to determine information on past manipulation data, particularly control variables of the vascular manipulation device, in particular a contact pressure. A cannulation robot can be designed to determine suitable cannulation procedural steps in the cannulating of the patient's blood vessel from such patient data (historical data), and preferably determine the cannulation to be performed, in particular the program parameters used in the program-controlled automatic cannulation, as a function of said historical data. Such historical data contains in particular the position of one or more of the patient's blood vessels as previously detected with the detection apparatus for measuring the position and/or dimensions of at least one subcutaneous patient blood vessel (vascular structure measuring device), and which is in particular available as patient data. Such historical data in particular contains information on the position and condition of prior puncture sites on the patient's body part which is in particular available as patient data.

The detection apparatus, respectively the control device of the detection apparatus, can be designed to perform an identification of the suitable subcutaneous blood vessel in the patient's body part for treatment, in particular for cannulation, and in particular a suitable insertion point on the skin for puncturing said blood vessel. The identification can be made for example in a control device via program-controlled analysis of an image obtained by the vascular structure measuring device.

In the sense of the invention, a "cannula" is a tubular body, in particular a rigid or flexible injection needle, having a lumen of a geometry and external dimensions suited for use in cannulation of a blood vessel. Preferably, the cannula comprises a hollow needle and a connector part.

The potential advantages as well as embodiments, further developments or variants of the invention cited previously also apply accordingly to the inventive cannulation robot.

A cannulation robot is an apparatus which automatically; i.e. at least intermittently or continuously, performs at least one cannulation process step in a patient blood vessel, or several or all intended process steps, without the intervention of a human operator, e.g. medical personnel. This thereby ensues in particular by the program parameters of the automated cannulation being accordingly selected by the system and/or by the user. One process step in the cannulation is in particular technically implemented by a component of the cannulation robot, e.g. a tool device, specifically configured for said process step and is selected from the group comprising the possible process steps P1, P2, P3 . . . , without this numbering defining a sequential ordering:

P1: Using an accessory kit to perform the cannulation which is selected prior to commencing the automated cannulation based on the registered patient identifier; this selection can have been made previously by means of an optional pick-and-place system of the system for selecting an accessory kit and/or equipping an accessory holder, in particular an accessory box; the accessory kit can have been provided beforehand as a function of the registered patient identifier by an optional sorting apparatus of the system selecting the accessories contained in the accessory kit from an optional storage apparatus of the system for storing accessories; the accessory kit can contain one or more medical accessories, in particular gauze, swabs, adhesive tape; the accessories of this accessory kit can be gathered as a function of the registered patient identifier and/or as a function of patient-specific treatment data derived from the registered patient identifier; the use of this accessory kit by the cannulation robot is a process step of the automated cannulation and can provide for the accessories of the accessory kit to be automatically extracted from predetermined positions of an accessory holder/box, in particular by the appropriate program parameters being selected as a function of the registered patient identifier and suitable for extraction; an optional pick-and-place device of the cannulation robot being in particular used to that end which is configured to extract the accessories out of the accessory holder and/or configured to equip one or more optional tool devices of the cannulation robot;

P2: Spatially fixating a part of the patient's body containing the blood vessel, in particular an arteriovenous fistula; the program parameters of the automated cannulation can be selected here as a function of the registered patient identifier, thus individual to each patient, these program parameters setting beforehand the position or the spacing of one or more optional fixation devices of the cannulation robot based on a previously determined location or on predetermined spacings on the patient's body part so as to achieve suitable fixation; the fixation taking place in the treatment chamber of the cannulation robot in which the patient's body part rests for the at least one ensuing cannulation;

P3: Using stored—in particular in a patient database—patient data in order to determine information on past cannulation process steps in the patient's vasculature (historical data), and preferably define the cannulation to occur, in particular the program parameters thereby used, based on this historical data; such historical data containing in particular the location of one or more of the patient's blood vessels previously measured by an optional measuring device of the cannulation robot for measuring the location and/or dimensions of at least one blood vessel under the patient's skin (vascular structure measuring device), and providing same in particular as patient data; such historical data containing in particular information on the location and condition of further puncture sites on the patient's body which is in particular provided as patient data; the vascular structure measuring device being able to be designed to detect the location and/or dimensions of at least one blood vessel under the patient's skin by means of ultrasound or by means of optical radiation;

P4: Identifying the blood vessel under the patient's skin suitable for the blood withdrawal, in particular selecting a suitable insertion site on the skin for the cannulation of said blood vessel; the program parameters of the automated cannulation can hereby be selected as a function of the registered patient identifier, thus individual to the specific patient, by the cannulation planned for the registered patient being selected on the basis of at least one patient-specific treatment parameter; for example with a patient planned for hemodialysis; a treatment parameter can encode the patient's necessity for hemodialysis; the cannulation of an arteriovenous blood vessel can be planned by evaluating the treatment parameter; same being identified; the identification can for example ensue in the control system by a program-controlled analysis of an image obtained by a vascular structure measuring device;

P5: Disinfecting the skin of the patient's body part containing the blood vessel; the program parameters of the automated cannulation can hereby be selected as a function of the registered patient identifier, thus individual to the patient, by a disinfecting process being specifically selected for the patient's type of skin or skin morphology which is for example characterized by the length of the treatment or the amount and nature of the disinfecting process employed; treatment data specific to the patient can also be considered; a disinfecting device which is optional with the cannulation robot or separate therefrom and equipped to perform the cited function can be used for the cited disinfection; the type of skin or skin morphology of the patient being preferably known in particular as patient data in the patient database;

P6: Physically treating the patient's body part containing the blood vessel in preparation for the cannulation, in particular stemming the blood flow of the body part, applying pressure to the body part, controlling the temperature of the body part, positioning the immobilized body part; the program parameters of the automated cannulation can hereby be selected as a function of the registered patient identifier, thus individual to the specific patient, by drawing on preparation data specific to the planned patient treatment, e.g. hemodialysis, or which can be taken from the patient database as known preparation data; this preparing for the cannulation of the body part being in particular performed by an optionally provided prepping device of the cannulation robot correspondingly configured for this purpose;

P7: Puncturing the blood vessel, in particular an arteriovenous fistula; preferably a first venipuncture and cannulation occurring automatically for withdrawing blood from the blood vessel and a second venipuncture and cannulation occurring automatically for the return of the blood, in particular in the case of hemodialysis; the program parameters of the automated cannulation can hereby be selected as a function of the registered patient identifier, thus individual to the specific patient, by the program parameters defining a patient-dependent motion control for a robotic tool arm optionally provided in the cannulation robot, by means of which a medical accessory such as for instance an injection needle can for example be grasped by the tool arm and positioned on the body part, with the injection needle having been previously selected and prepared specific to the patient; two cannulation robots can be set up for puncturing blood vessels at different parts of the body by, for example, a first cannulation robot being configured for cannulation on an arm and a second cannulation robot being configured for cannulation on a leg; the selection of the appropriate cannulation robot can ensue in patient-specific and/or treatment-specific manner; using one cannulation robot each on both respective arms (legs) is for example also possible.

P8: Withdrawing blood from the cannulated blood vessel and transporting the blood in at least one blood transport device or in at least one sample container; the program parameters of the automated cannulation can hereby be selected as a function of the registered patient identifier, thus individual to the specific patient, by a suitable blood transport device or suitable sample container being preselected as a function of patient-specific treatment data and then utilized in suitable manner by the cannulation robot; the cannulation robot and the control system can be configured thereto by an appropriate selection of the program parameters to provide at least one sample container based on treatment data for the subsequent, preferably automatic and system-controlled, treatment, in particular diagnostics;

P9: The grasping of a cannula by a gripper apparatus of the cannulation robot.

The term "cannulation" refers to a procedure in which a cannula is inserted into the blood vessel in the patient's body part by puncturing the skin and venipuncturing the blood vessel wall so that the distal end of the cannula is disposed in the blood vessel and the proximal end of the cannula is disposed on the outside of the body part so that a fluid connection can be established between the cannula and the blood vessel, by means of which fluid, in particular blood and/or fluid media, can be exchanged via the fluid connection. The "exchange" of fluid in this context means that fluid from the patient's blood circulation is conveyed to an extracorporeal fluid system, i.e. situated external of the patient's body, in particular for fluid storage or fluid conduction, and/or includes conveying fluid from the extracorporeal system into the blood circulation.

Chronically ill patients need regularly repeated vasculature cannulation in order to ensure the necessary treatment. One such chronic illness is kidney failure which leads, among other things, to the loss of the blood's natural purifying function. Technical solutions can be substituted in its place. Hemodialysis devices are extracorporeal filtering units serving as artificial kidneys into which the blood of the patent is conducted in order to be cleansed and treated before being returned to the patient's blood circulation. Blood is normally withdrawn and returned via an artificial subcutaneous connection surgically created between a vein and an artery in an arm or a leg of the patient. This connection can be composed of a section of the patient's own vasculature prepared for same or can consist of an artificial material and is referred to as a fistula or arteriovenous fistula respectively (AV fistula, AVF).

The most commonly used permanent vascular access in chronic hemodialysis patients is a native arteriovenous fistula. After the native arteriovenous fistula is placed, it become stronger due to the increased blood flow, whereby repeated cannulation for the dialysis treatment becomes easier.

Hemodialysis must be performed regularly, typically a few days apart. This leads to high mechanical stress on the blood vessel or arteriovenous fistula respectively. Different techniques are known to create access to a blood vessel or arteriovenous fistula respectively, these aiming to be as gentle as possible on the vessel over the course of the repeated cannulation. In rope ladder cannulation, a new cannulation site located at a distance from the previous site, e.g. about 2 cm, is sought for each treatment. In this method, the series of punctures are usually started at the lower end of the vessel and then continue upward until reaching the upper end and the process then started again from below. The practitioner must thereby precisely follow the positioning pattern so as to allow the venipunctured vessel sites to heal. In contrast, in the buttonhole technique, a needle is always inserted into the exact same spot at the exact same angle. Over time, a scar tunnel thus develops which continually displaces the thrombus forming in cannulation and thus becomes more resilient. It has been found that buttonhole technique results can be improved if the cannulation is always performed by the same treatment personnel. For this reason, the use of a cannulation robot is particularly advantageous.

Due to the frequency of cannulation with hemodialysis patients, the arteriovenous fistula is subject in general to high stress, independent of the venipuncture technique, same which can lead to changes in the surface of the skin and the condition of the arteriovenous fistula and how they progress. The present invention allows regulated optimizing of the position and/or dimensions of the blood vessel so that in particular an automatic cannulation can be realized gently, quickly and efficiently.

One advantage of the cannulation robot with detection apparatus can additionally be seen in that, in particular when treating chronic illnesses—in particular with hemodialysis patients—, the automated cannulation can reduce the workload of the medical personnel and/or provide a consistently high cannulation precision, whereby in particular treatment quality and/or treatment safety can be increased.

The potential advantages as well as embodiments, further developments or variants of the aspects of the invention cited previously also apply accordingly to the inventive method. Inversely, potential advantages as well as embodiments, further developments or variants of the method also apply accordingly to the preceding aspects of the invention.

As defined by the invention, "configured" refers to an apparatus not only being in principle suited to fulfill a specific function—for instance only after a specific program code has been loaded; i.e. the apparatus programmed, or the apparatus formed in a specific way—, but the apparatus already possesses all the means necessary in order to actually fulfill the function. Preferably, the apparatus is to that end already programmed with a program code for said function and/or already configured and/or arranged and/or exhibits such a configuration thereto that the apparatus actually fulfills the function.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

A "group of treatments" in the sense of the invention can be respective specific operations, therapy for a specific illness, the initial examination of a patient, or a dialysis treatment which in turn can comprise sub-groups, in particular hemodialysis, hemofil-tration, hemodiafiltration, hemoperfusion or peritoneal dialysis treatments. Apheresis constitutes a further possible treatment group.

As defined by the invention, an "individual involved in the treatment" can in particular be understood as an attending person, for instance a physician, or an individual providing treatment support, for instance a nurse. In particular, the patient to be treated can himself also be an individual involved in the treatment or an attending person.

A data processing control device of the detection apparatus and/or the cannulation robot comprises a data processing apparatus.

To be understood by a "data processing apparatus" is an apparatus configured to process data; i.e. in particular to receive data, store received data, read out stored data, transform received and/or stored and/or read data by means of logical and/or mathematical operations, store transformed data, and/or output transformed and/or read data. Preferably, such a data processing device is programmable; i.e. a program code in particular at least partially specifies the method for processing the data and at least part of said program code is modifiable.

Preferably, the data processing apparatus is a commercially available microprocessor or computer. Further preferentially, the data processing apparatus comprises at least one data processor—i.e. a central processing unit—, a non-volatile—i.e. in particular permanent—data storage, in particular a hard disk, a read-only memory (ROM) or a drive with a data medium, as well as at least one hardware interface. The data processing apparatus also preferably comprises a volatile electrical data storage, in particular as main memory, preferably a semiconductor memory, in particular with integrated capacitors and/or flip-flops (bistable multivibrators) for data storage, for instance dynamic RAM or static RAM.

In the sense of the invention, a "data storage apparatus" or "data storage device" is an apparatus for storing data. Same is in particular designed to form a data link with a further apparatus, particularly a data processing apparatus, and/or comprises a data link to the further apparatus, wherein data can be transmitted to the data storage apparatus from the further apparatus for storage by means of the data link and/or data can be transmitted from the data storage apparatus to the further apparatus for retrieval. Preferably, the data storage apparatus comprises at least one non-volatile data storage. Also preferably, the data storage apparatus comprises at least one volatile electrical data storage.

A data link connects in particular two data processing units, in particular two data processing devices or apparatus, in a way so as to enable the exchange of data between the units, either unidirectionally or bidirectionally. The data link can be realized in wired or wireless manner, in particular as a radio link. A remote data link connects in particular two data processing units, particularly two data processing devices, disposed at a distance from one another, thus not being component parts of the same device, in particular the same user interface device or the same control system, if the cited devices are realized as separate units. A data link, in particular remote data link, of one device to another device is preferably realized by a direct connection between the two devices or by an indirect connection of the two devices such that a third device is connected between the two devices in order to pass on the data. A remote data link can in particular be realized by a network of computers with which the devices connected by the remote data link are interconnected via the network. The network can be a restricted network, e.g. an intranet, or global network, in particular a WAN and/or the internet.

In the sense of the invention, an "interface device" serves the connection of two units—in particular including systems, apparatus, devices or mechanisms, particularly having such units—, respectively capable of processing signals, in particular information, particularly data, thus in particular sending and/or receiving. An interface device can comprise at least one hardware interface and in particular be integrated into a physical device unit as a component part.

The term "treatment of a laboratory sample" in particular means that a laboratory sample, in particular a sample or a volume of blood, is moved and/or transported and/or examined and/or physically, chemically, biochemically or in some other way modified, in particular as regards its composition.

The invention further relates to a method for the automatic detection and manipulation of a blood vessel under the skin of a part of a patient's body, in particular a method for operating a detection apparatus, particularly a detection apparatus according to the invention, comprising the steps of:—Detecting the position and/or dimensions of a blood vessel in a treatment chamber by measuring vascular structure data of the blood vessel in the treatment chamber;—optionally: Comparing the vascular structure data to comparative data, which in particular contains predetermined reference values on the position and/or dimension of the blood vessel; optionally:—Applying a criterion in order to determine a result from said comparison;—Changing the position and/or dimension of the blood vessel by means of a vascular manipulation device, controlled by a control device as a function of the vascular structure data.

Preferably, the detection apparatus, in particular a treatment apparatus comprising the detection apparatus, comprises at least one of the following components: a user interface device, with which a user can make at least one data input which is processed by the control device or its program code, and/or with which information can be output to the user, wherein the user interface device can comprise a display, in particular a touchscreen, speaker and/or input device such as e.g. a keyboard; a housing, into which the control device, treatment chamber, vascular structure measuring device and/or the vascular manipulation device is/are integrated, wherein the housing can comprise an opening or a doorway device providing access to the treatment chamber in order to receive the user's body part; a base, in particular a supporting frame bearing the components of the detection apparatus or at least one of said components; a power supply system for supplying power to the electrical components of the detection apparatus; a communication device for exchanging data with an external data processing apparatus, in particular via remote data link.

The invention further relates to a data processing system comprising a detection apparatus according to the present description and/or a treatment apparatus comprising said detection apparatus, in particular a cannulation robot, and at least one external data processing apparatus networked with the detection apparatus and/or the treatment apparatus for the exchange of data, in particular over a data link or a remote data link. The system can further comprise a data storage apparatus as a component, same being networked to at least one other system component for exchanging data. The data storage apparatus can contain a patient database in which patient data is stored and able to be retrieved.

The invention further relates to a method for the automatic cannulation of a blood vessel under the skin of a patient's body part, in particular a method for operating a cannulation robot, particularly a cannulation robot in accordance with the invention, comprising the steps of the inventive method for automatically detecting and manipulating a blood vessel under the skin of a patient's body part, and comprising the step(s) of:—Automatic cannulation of the blood vessel manipulated by the vascular manipulation device;—optionally: Performing said cannulation within a predetermined limited interval of time.

Further advantages, features and possible applications of the present invention are yielded by the following detailed description of at least one example embodiment and/or by the figures. Unless otherwise described or contextually indicated otherwise, the same reference numerals are substantially used to identify equivalent components in the embodiments. The figures show the following example embodiments of the invention:

FIGS. 1 to 5 in each case show a side view of the inventive detection apparatus according to a preferential example embodiment, with the vascular manipulation device in each case realized as a pressing device.

FIGS. 6 to 8 in each case show a side view of the inventive detection apparatus according to a preferential example embodiment, with the vascular manipulation device in each case realized as a heat transfer device.

Figure 1:
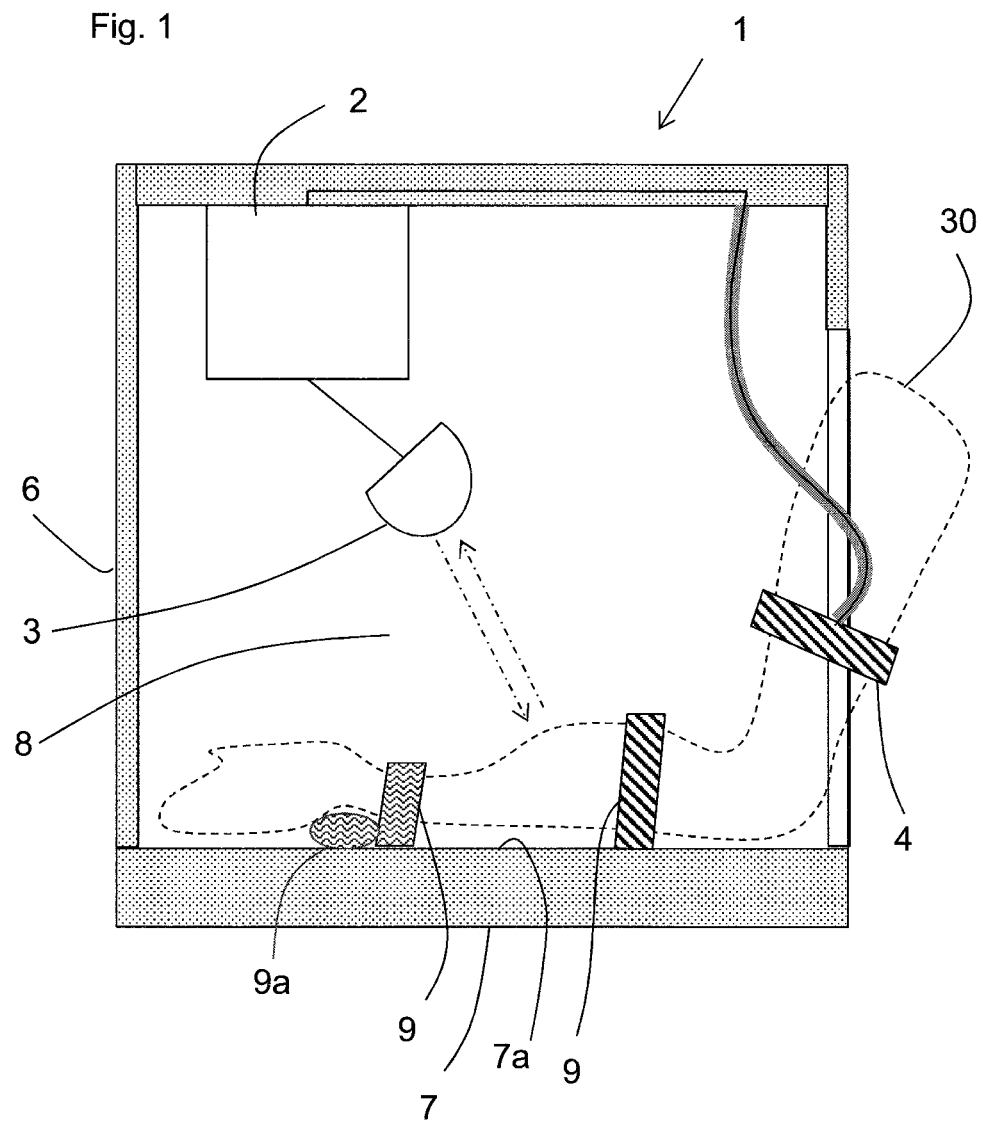
Figure 12:
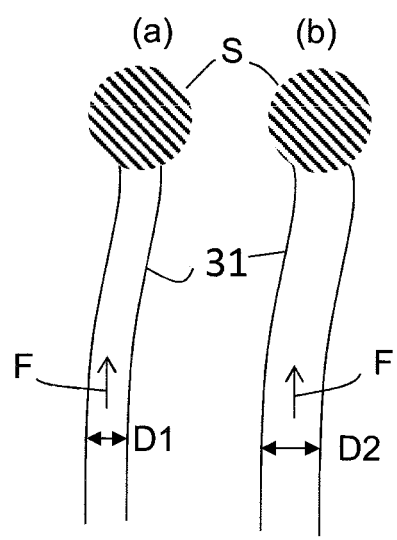
FIG. 12 shows an example of a change in the dimension of a blood vessel, effected by a detection apparatus according to the invention.
Figure 13:
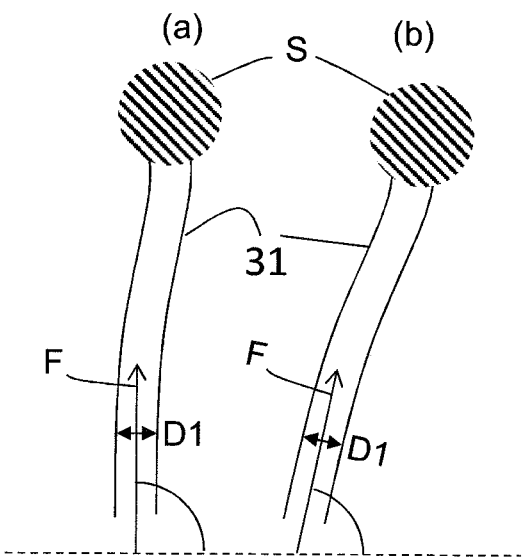
FIG. 13 shows an example of a change in the position of a blood vessel, effected by a detection apparatus according to the invention.

FIG. 1 shows a detection apparatus 1 for the detecting and manipulating of a blood vessel under the skin of a part of a patient's body. The arm 30 of the patient is immobilized by means of fixation straps 9 on a body part support 7*a*, here an armrest, padded by means of body part guiding padding 9*a*. The blood vessel 31, see FIGS. 12, 13, can in particular be an arteriovenous fistula which the patient has due to hemodialysis treatment. A complete blockade or partial congestion of the blood vessel at a position S, which is situated upstream in flow direction F relative to the section of the blood vessel to be detected, can improve the detection and in particular subsequent treatment, particularly cannulation, of the blood vessel section.

The detection apparatus has a base platform 7 with an open frame 6 and a treatment chamber 8 for accommodating the body part. The detection apparatus 1 comprises a data processing control device 2 and a vascular structure measuring device 3 for detecting the position and/or dimensions of the blood vessel in the treatment chamber by measuring vascular structure data. The vascular structure measuring device 3 is in the present case an ultrasonic measuring device.

The detection apparatus 1 additionally comprises a vascular manipulation device 4 configured as a pressing device for changing the dimension of the blood vessel. The pressing device 4 is an inflatable hollow arm cuff 4 and comprises an electrically operated air pump (not shown) to increase the pressure in the hollow arm cuff 4 until a specific blood vessel position and/or thickness is reached. The hollow arm cuff 4 can comprise a force or respectively pressure sensor (not shown) in order to measure the pressure applied by the hollow arm cuff on the body part, here the upper arm, and to stop the vascular manipulation upon an allowable maximum pressure being exceeded.

The control device 2 is designed to control the vascular manipulation device 4 as a function of the vascular structure data measured by means of the vascular structure measuring device 3. The control device determines from the vascular structure data whether the blood vessel is of a predetermined thickness D2 suitable for a subsequent treatment, in particular an automatic cannulation of said blood vessel at said thickness. The control device 2 is thereby designed to increase the contact pressure in a case of meeting the criterion of the blood vessel's measured thickness D1 being less than D2. The pressure can be increased in incremental steps under continuous measurement by means of the vascular structure measuring device 3. Alternatively or additionally, the increase in pressure can entail a predetermined, larger pressure increase step based on empirical values applied, for example, prior to an incremental increase or reduction of the contact pressure in order to accelerate the success of the blood stemming measure.

As soon as thickness D2 is detected subsequent the increase (and/or reduction) in the contact pressure on the blood vessel, the change in contact pressure is stopped or, respectively, the contact pressure is regulated such that the measured thickness remains constant at D2, at least for a predetermined or controlled interval of time. A further treatment of the blood vessel, in particular a cannulation, can occur within this time interval.

Figure 2:
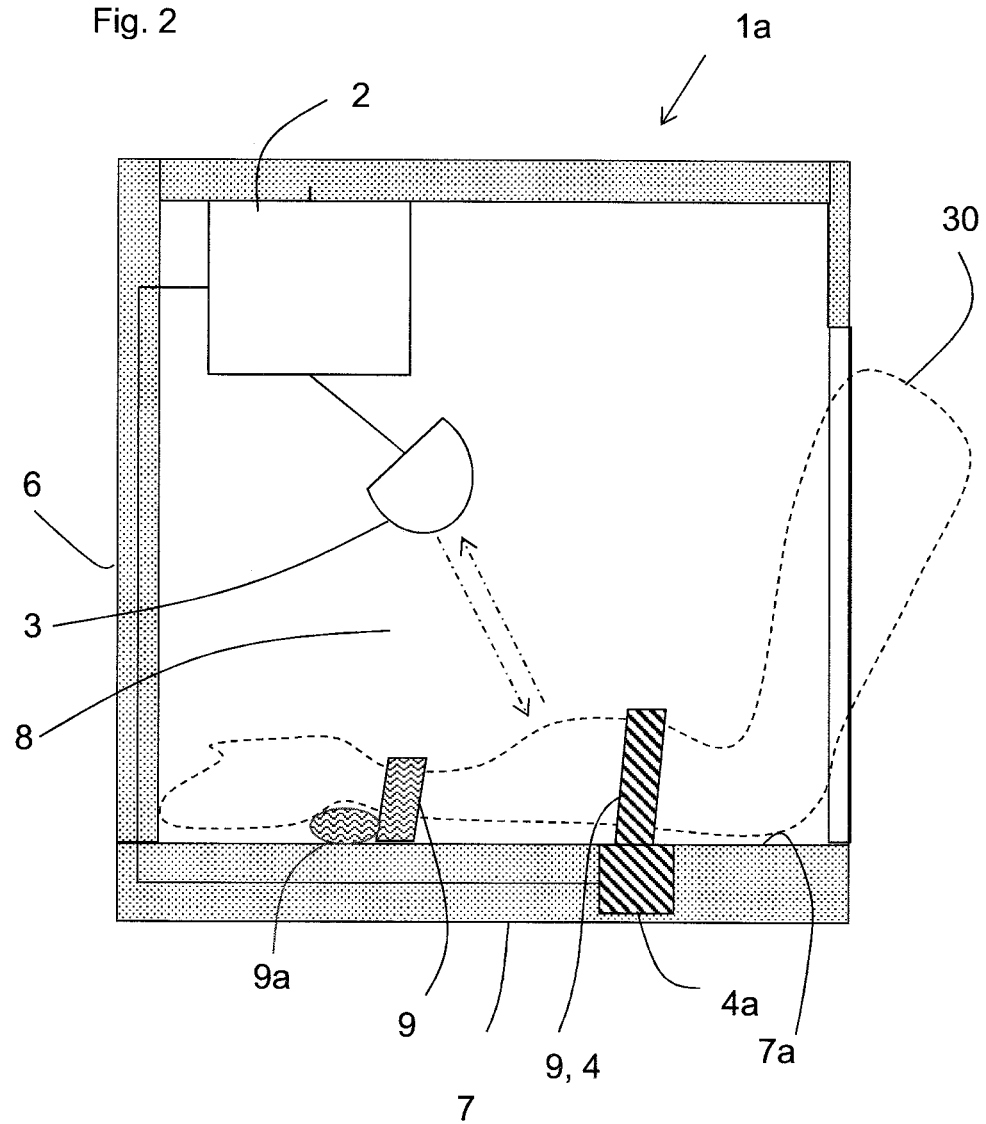

Detection apparatus 1*a* is shown in FIG. 2, its vascular manipulation device 4 likewise a pressing device, in particular a ligature 4 wrapped around the arm 30 and able to be lashed by an electric motor 4*a*, which concurrently serves as a fixation strap to immobilize the arm on the rest 7*a*. The electric motor 4*a* is controlled by the control device such that the blood vessel attains and maintains the desired thickness D2.

Figure 3:
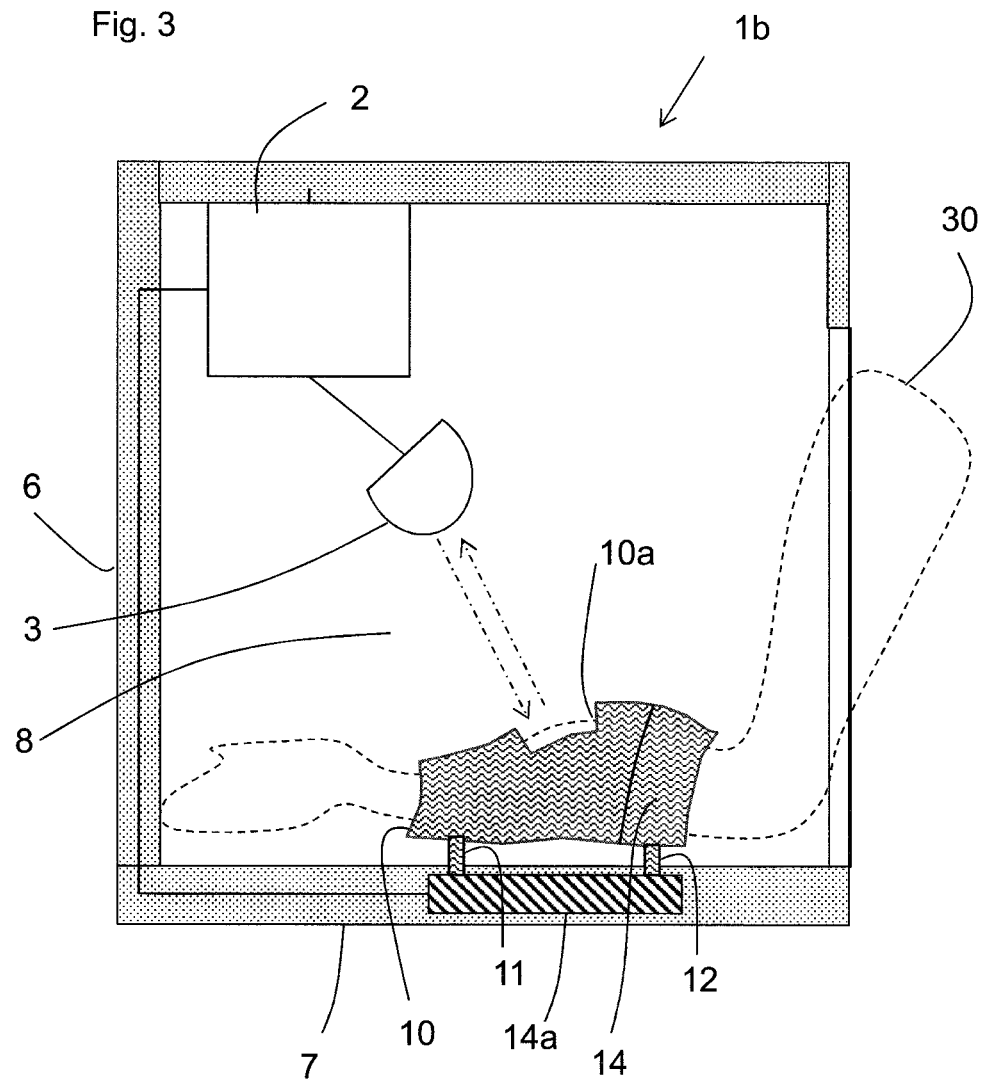

Detection apparatus 1*b* is shown in FIG. 3, its vascular manipulation device 14 likewise a pressing device, in particular a tubing cuff 10 wrapped around the arm 30 and inflatable by means of an electric motor 14*a* which is or can be fixed to the rest. The tubing cuff 10 comprises a separate pressure region 14 in the proximal area of the arm able to be pressurized via the separate air supply section 12 in which a contact pressure can be precisely adjusted. The tubing cuff 10 concurrently serves as a fixation sleeve in that the rest of the tubing cuff outside of pressure region 14 can be sufficiently filled with air via air supply section 11 in order to immobilize the arm. The electric motor 14*a* for pumping the air is controlled by the control device such that the blood vessel attains and maintains the desired thickness D2.

Figure 4:
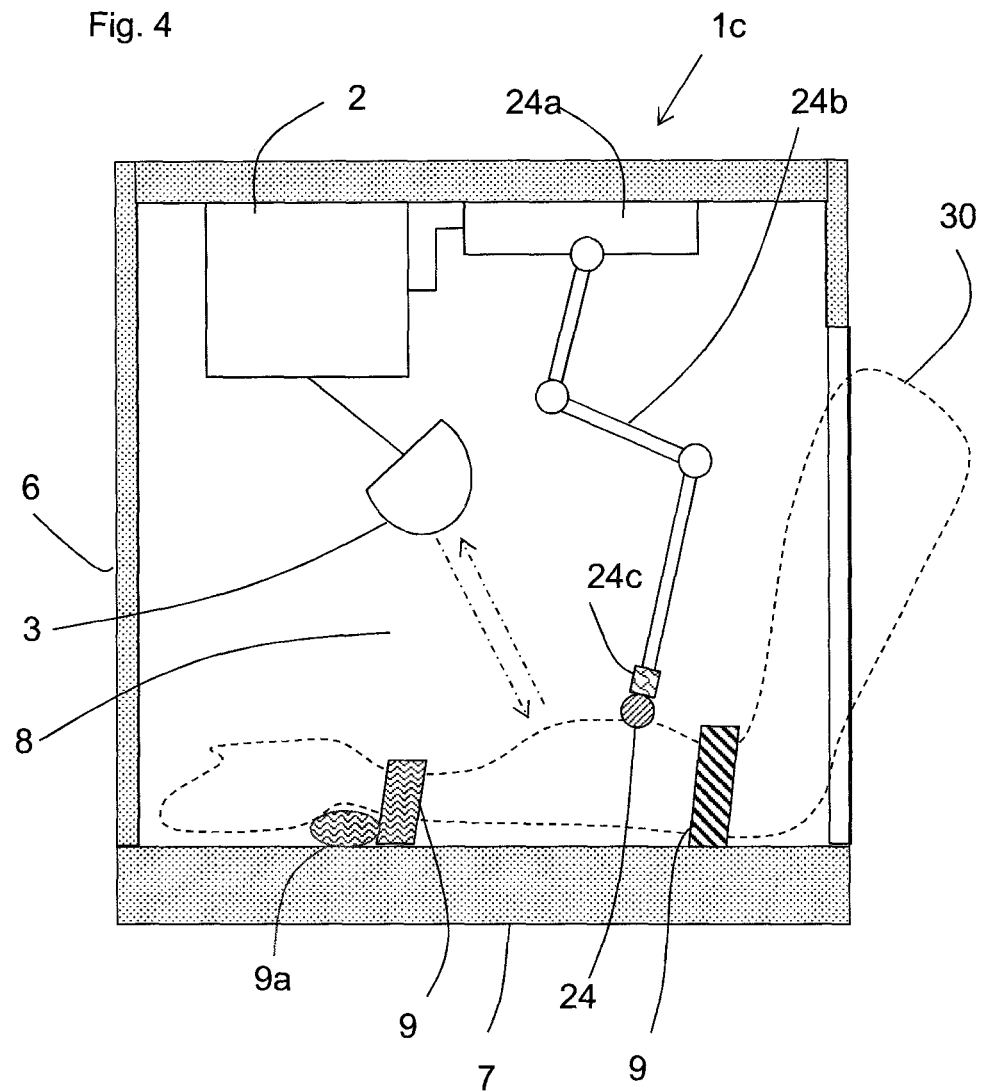

Detection apparatus 1*c* is shown in FIG. 4, its vascular manipulation device 4 likewise a pressing device, comprising a movable holding device 24*b* for the pressing head 24, in particular a jointed arm 24*b*, controlled and moved by means of a drive unit 24*a* of the pressing head. The pressing head here has a contact area of approx. 5 cm² in contact with the skin over the blood vessel to be stemmed and which is pressed into the arm. In order to determine the applied force and to stop or regulate the action of the vascular manipulation device 24 if needed, a force sensor 24*c* can be provided on the holding device 24*b*. The drive 24*a* is controlled by the control device 2 such that the blood vessel attains and maintains the desired thickness D2.

Figure 5:
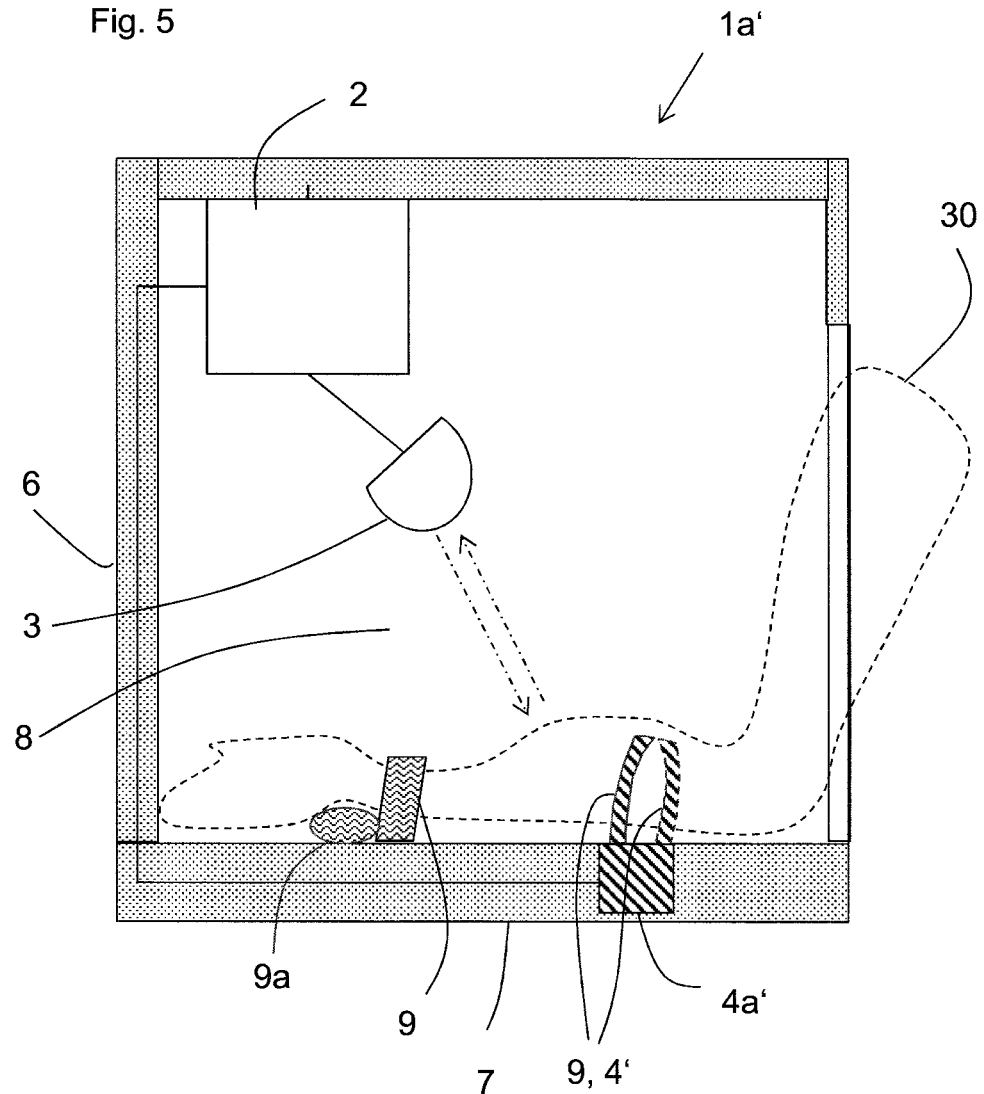

Detection apparatus 1*a'* is shown in FIG. 5, its vascular manipulation device 4' likewise a pressing device comprising two movable pressing and retaining clamping arms 4' which are placed as desired around the arm 30 and pressed onto the arm by an electric motor 4*a'*. The section of tissue containing the blood vessel can thereby be pressed between the ends of the clamping arms 4' in a radially outward direction away from the body part, whereby on one hand the desired blood congestion is achieved and, on the other hand, the blood vessel is accessible and additionally fixed. The electric motor 4*a'* is controlled by the control device 2 such that the blood vessel attains the desired thickness D2.

Figure 6:
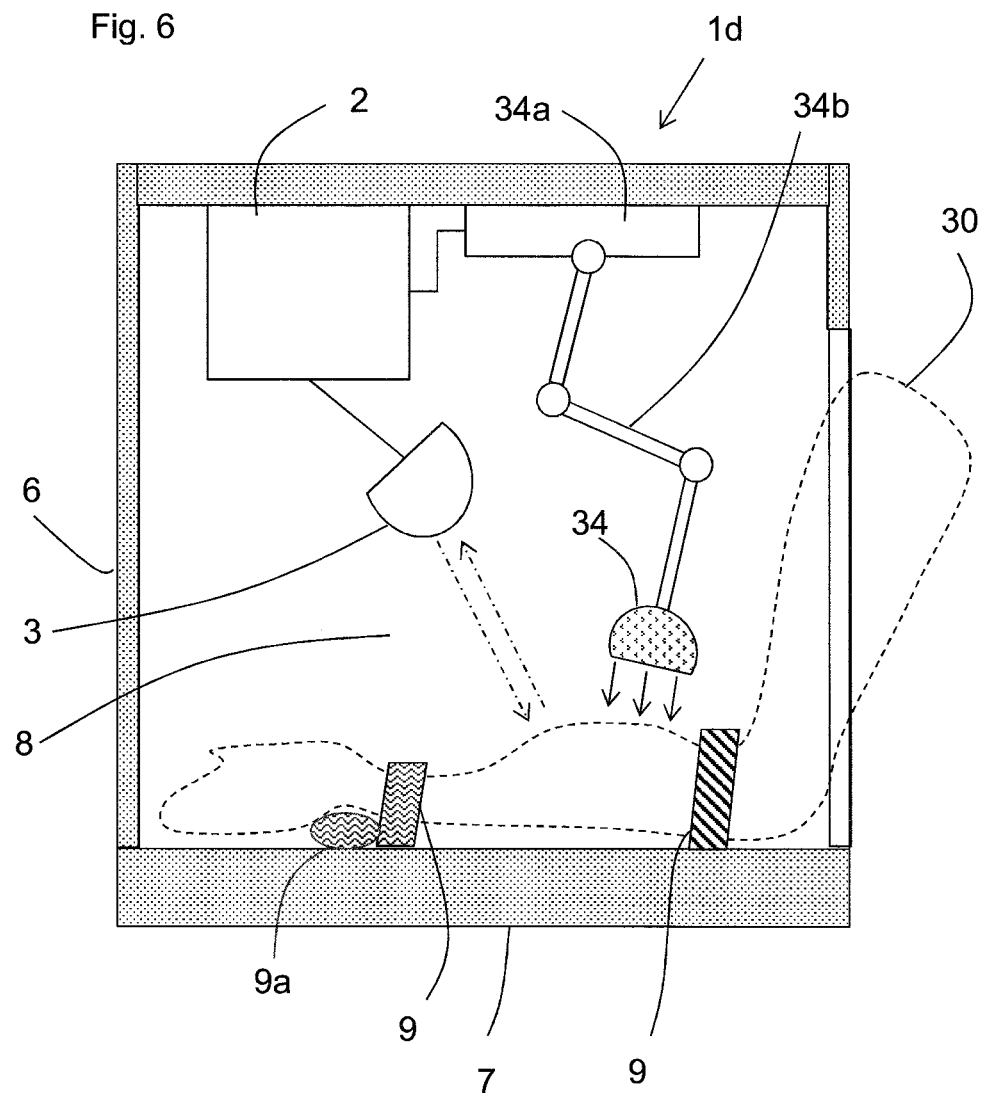

FIG. 6 shows detection apparatus 1*d* in which the vascular manipulation device is configured as heat transfer device 34. The heat transfer device 34 is here an infrared lamp attached to the movable holding device 34*b*, in particular the jointed arm 34*b*, its position and/or output set by means of drive and control unit 34*a* of the infrared lamp (output measured in kW). The position, output and/or contact period of the heat transfer device 34 is set and/or controlled such that the blood vessel attains and in particular maintains the desired thickness D2 due to the thermally increased blood circulation.

Figure 7:
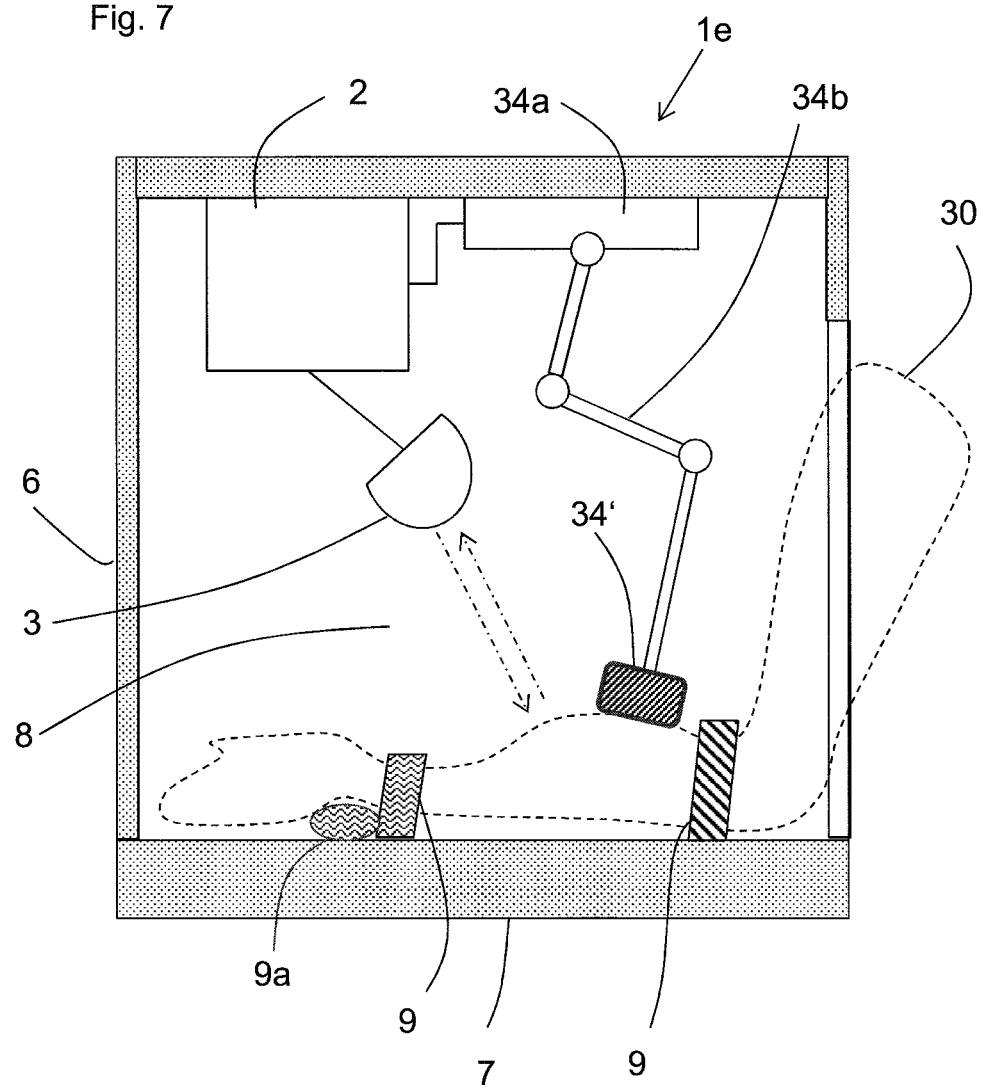

FIG. 7 shows detection apparatus 1*e* in which the vascular manipulation device is configured as heat transfer device 34'. The heat transfer device 34' is here a skin-contacting heat transfer element 34' with integrated temperature control device, e.g. a Peltier element, attached to the movable holding device 34*b*, in particular the jointed arm 34*b*. The position of the heat transfer element and/or the output of the temperature control device can be set by the drive and control unit 34*a*. The position, output and/or contact period of the heat transfer device 34' is set and/or controlled such that the blood vessel attains and in particular maintains the desired thickness D2 due to the thermally increased blood circulation.

Figure 8:
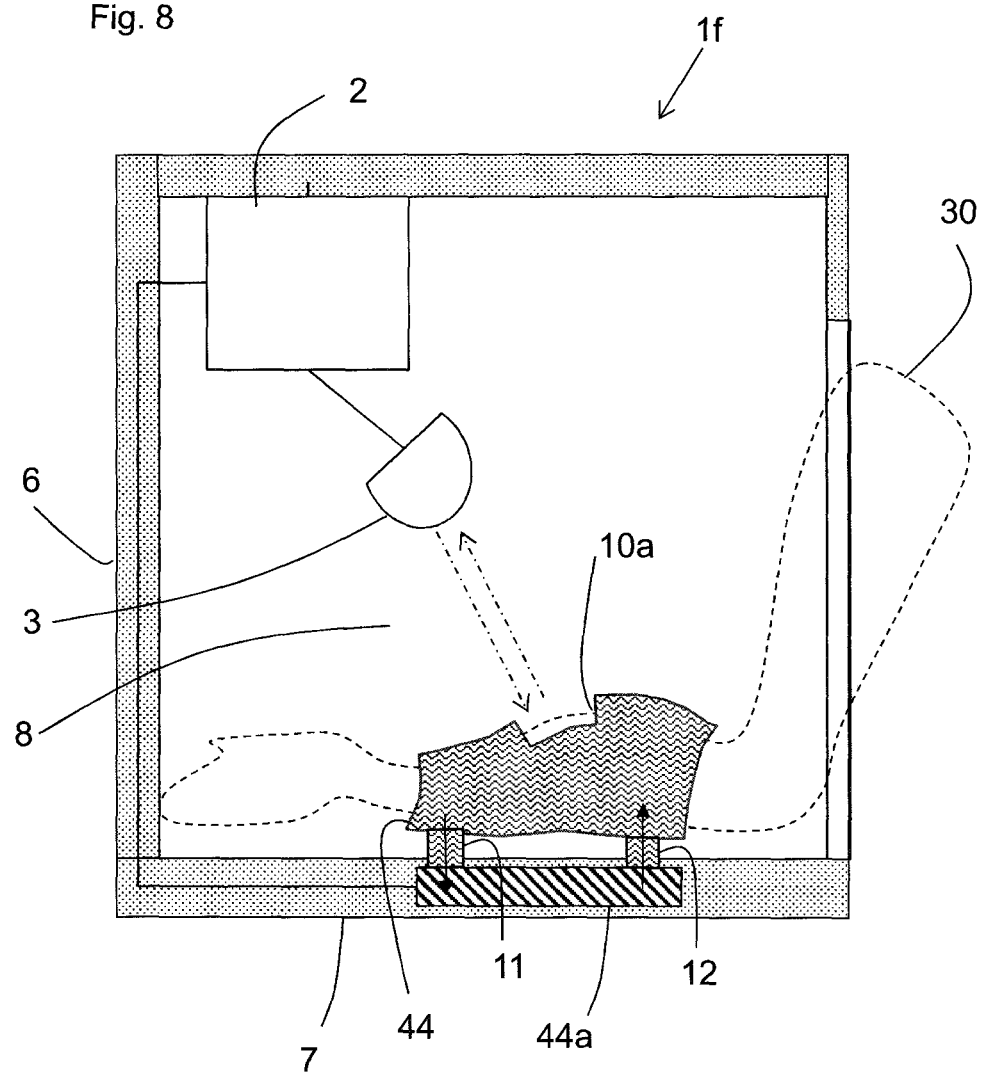

FIG. 8 shows detection apparatus 1*f* in which the vascular manipulation device is configured as heat transfer device 44. The heat transfer device 44 is here a body part cuff 44 through which a heat transfer fluid can flow, which here encircles the arm apart from window 10*a*. The fluid medium, preferably water, is temperature controlled by means of the temperature control device, e.g. electrical resistance device, in the control 44*a* of the arm cuff 44. The temperature-controlled medium is pumped in through the arm cuff 44 via access port 12 in the control 44*a* by means of a pump (not shown). A channel system can be provided in the tubing cuff, in particular a spiral line duct running around the arm or a serpentine line duct. The channel system distributes the medium over the surface of the arm cuff 44 in order to evenly warm the arm 30 in the present case. The medium is discharged again through drainage port 11 of the arm cuff 44 and returned back into the control 44*a* for circulation. The output of the temperature control device can be set by the control 44*a*. The output of the heat transfer device 44 is set and/or controlled such that the blood vessel attains and in particular maintains the desired thickness D2 due to the thermally increased blood circulation.

Figure 9:
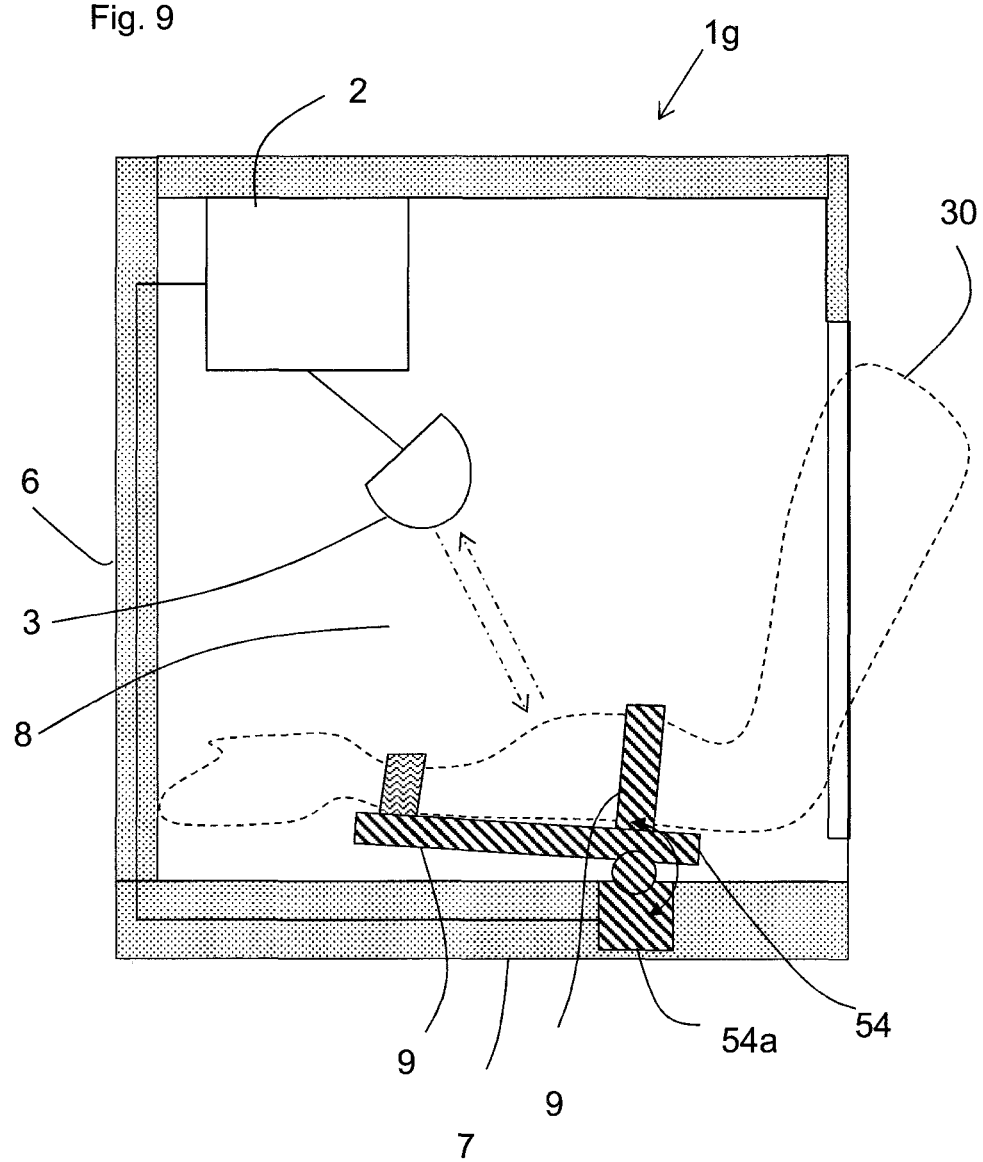
FIG. 9 shows a side view of the inventive detection apparatus according to a preferential example embodiment in which the vascular manipulation device is realized as a movable supporting device for the movable support of the arm.

FIG. 9 shows detection apparatus 1*g* in which the vascular manipulation device 54 is configured as a movable supporting device for movably supporting the arm. The movable supporting device comprises a platform serving as a support surface for the arm which is able to be rotated by means of a pivot and on which said arm can additionally be immobilized by fixation straps 9. The control device 2 controls the rotation about one or more axes by the electric motor provided in the control 54*a* such that the blood vessel contained and detected in the arm 30 attains the desired position (see FIG. 13).

Figure 10:
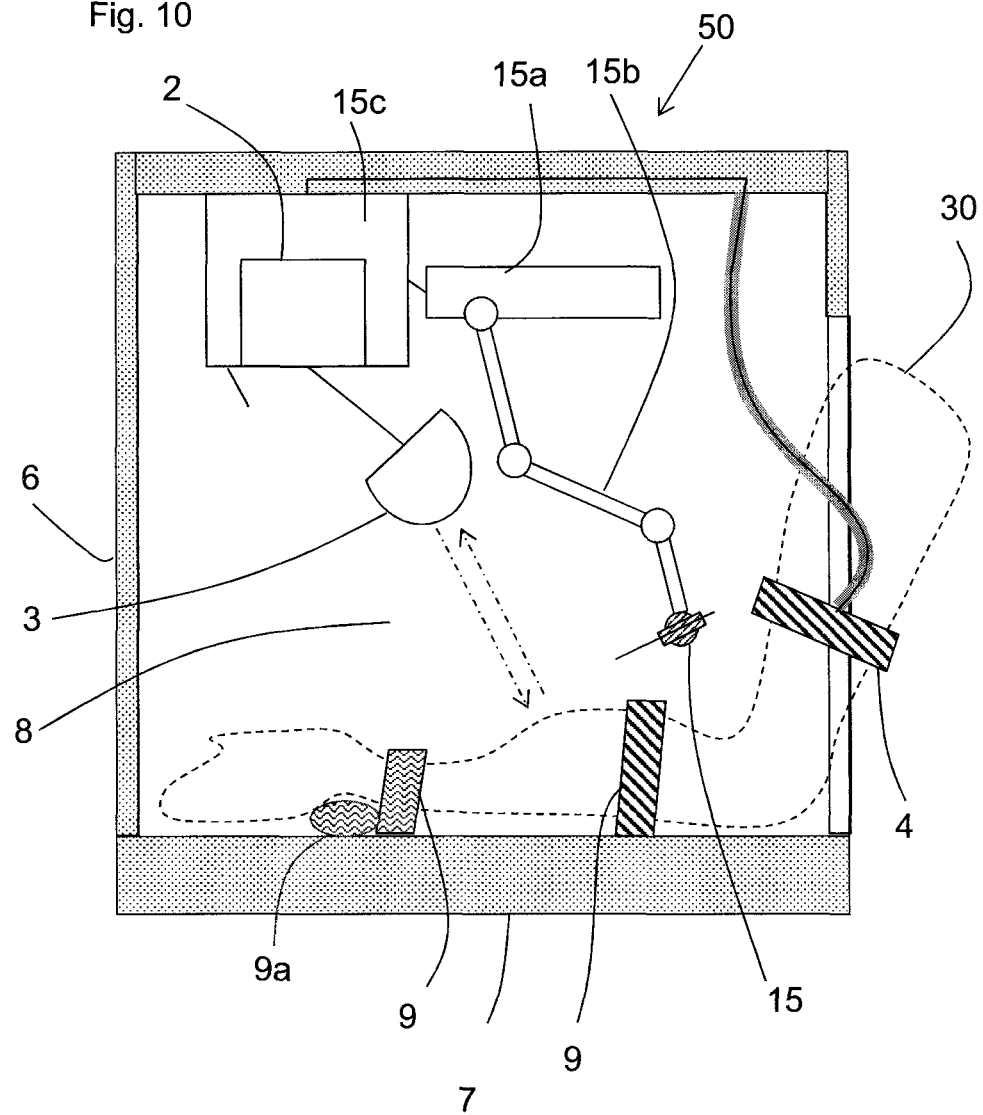
FIG. 10 shows a side view of the inventive cannulation robot according to a preferential example embodiment as equipped with an inventive detection apparatus.

FIG. 10 shows the cannulation robot 50 according to the invention which comprises an inventive detection apparatus 1. The cannulation robot 50 comprises a robotic jointed arm 15*b* and a motor with motor control 15*a*, its tool head 15 bearing a cannula with which the automatic puncturing and cannulation of the blood vessel detected by the vascular structure measuring device 3 and manipulated by the vascular manipulation device 4 is effected. The control device 2 of the cannulation robot contains the control device 2 of the detection apparatus. Functions of the cannulation robot and the detection apparatus can be implemented by program code executed by the processor of the control device 2.

Figure 11:
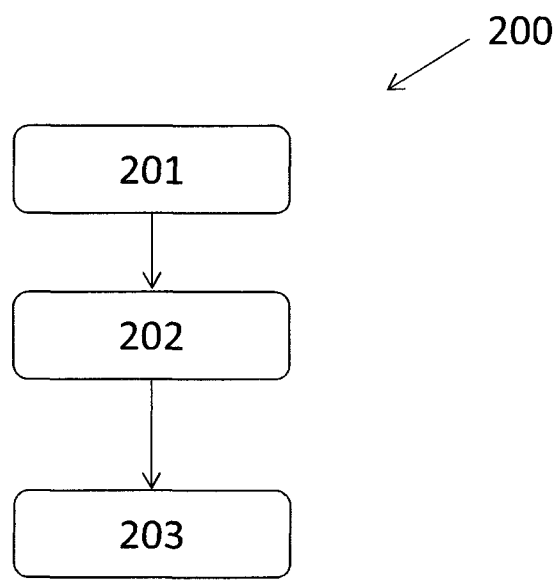
FIG. 11 shows an example embodiment of the method according to the invention.

FIG. 11 shows an example embodiment of the inventive method for operating a detection apparatus, comprising the steps: Step 201—Detecting the position and/or dimensions of a blood vessel in a treatment chamber by measurement of vascular structure data of the blood vessel in the treatment chamber;—optional Step 202: Comparing the vascular structure data to comparative data which in particular contains predefined reference values on the position and/or dimension of the blood vessel; Step 203—Changing position and/or dimension of the blood vessel by means of a vascular manipulation device controlled by a control device 2 as a function of the vascular structure data.

The invention claimed is:

1. A detection apparatus for detecting and manipulating a blood vessel under the skin of a body part of a patient, comprising
    a treatment chamber for accommodating the body part;
    a data processing control device;
    a vascular structure measuring device for detecting a position and/or dimensions of the blood vessel in the treatment chamber by measurement of vascular structure data of the blood vessel in the treatment chamber; and
    a vascular manipulation device for changing the position and/or the dimensions of the blood vessel,
        wherein the vascular manipulation device comprises a movable holding device and a pressing head,
        the movable holding device is a robotic arm for placing the pressing head onto the body part,
        the data processing control device is designed to control the vascular manipulation device as a function of the vascular structure data,
        the data processing control device is designed to determine from the vascular structure data whether the blood vessel is of a predetermined thickness, and
        the data processing control device is designed to control the vascular manipulation device such that the blood vessel attains the predetermined thickness and maintains the predetermined thickness for at least a predetermined interval of time.

2. The detection apparatus according to claim 1, wherein the vascular manipulation device is designed as a pressing device and a control of the pressing device is effected by a setting of a contact pressure.

3. The detection apparatus according to claim 2, wherein the pressing device comprises a force sensor or a pressure sensor for measuring the contact pressure.

4. The detection apparatus according to claim 3, wherein the data processing control device is designed such that a predetermined or a data processing control device-determined maximum contact pressure is not exceeded.

5. The detection apparatus according to claim 1, wherein the vascular structure measuring device is designed as an image capture device and comprises an optical measurement or is based on an ultrasound measurement.

6. The detection apparatus according to claim 1, wherein the data processing control device is designed to regulate the vascular manipulation device as the function of the vascular structure data.

7. The detection apparatus according to claim 1, wherein the data processing control device is designed to perform a change of the position and/or the dimensions of the blood vessel within a predetermined time interval.

8. A cannulation robot comprising the detection apparatus of claim 1 and being arranged for an automatic cannulation of a blood vessel of the body part of the patient detected by the detection apparatus.

9. A method for operating a detection apparatus, comprising:
   detecting a position and/or dimensions of a blood vessel under the skin of a body part of a patient in a treatment chamber by measuring vascular structure data of the blood vessel in the treatment chamber;
   changing the position and/or the dimensions of the blood vessel by means of a vascular manipulation device that is controlled by a data processing control device as a function of the vascular structure data, wherein
      the vascular manipulation device comprises a movable holding device and a pressing head,
      the movable holding device is a robotic arm for placing the pressing head onto the body part,
      the changing the position and/or the dimensions of the blood vessel comprises pressing the body part of the patient with the pressing head,
      it is determined from the vascular structure data, by means of the data processing control device, whether the blood vessel is of a predetermined thickness, and
      the vascular manipulation device is controlled, by means of the data processing control device, such that the blood vessel attains the predetermined thickness and maintains the predetermined thickness for at least a predetermined interval of time.

10. A method for a cannulation of the blood vessel, wherein the blood vessel is disposed under the skin of a body part of a patient, wherein the method comprises the method steps according to claim 9 and, subsequent to the changing the position and/or the dimensions of the blood vessel by means of the vascular manipulation device, automatically cannulating the manipulated blood vessel.

\* \* \* \* \*